United States Patent
Ye et al.

(10) Patent No.: US 8,208,599 B2
(45) Date of Patent: Jun. 26, 2012

(54) ITERATIVE RECONSTRUCTION WITH ENHANCED NOISE CONTROL FILTERING

(75) Inventors: Jinghan Ye, Fremont, CA (US); Lingxiong Shao, Saratoga, CA (US); Zuo Zhao, Palo Alto, CA (US); Mary K. Durbin, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1127 days.

(21) Appl. No.: 12/067,185

(22) PCT Filed: Aug. 21, 2006

(86) PCT No.: PCT/IB2006/052881
§ 371 (c)(1),
(2), (4) Date: Mar. 18, 2008

(87) PCT Pub. No.: WO2007/034342
PCT Pub. Date: Mar. 29, 2007

(65) Prior Publication Data
US 2009/0232375 A1    Sep. 17, 2009

Related U.S. Application Data

(60) Provisional application No. 60/720,431, filed on Sep. 26, 2005.

(51) Int. Cl.
*G06K 9/00* (2006.01)
(52) U.S. Cl. .......................................... 378/4; 382/131
(58) Field of Classification Search ....... 378/4; 382/131
See application file for complete search history.

(56) References Cited

U.S. PATENT DOCUMENTS

| | | | |
|---|---|---|---|
| 6,310,968 B1 * | 10/2001 | Hawkins et al. | 382/131 |
| 6,426,988 B2 * | 7/2002 | Yamada et al. | 378/4 |
| 6,507,633 B1 * | 1/2003 | Elbakri et al. | 378/8 |
| 6,754,298 B2 * | 6/2004 | Fessler | 378/4 |
| 7,085,405 B1 * | 8/2006 | Levkovitz et al. | 382/131 |
| 2005/0259780 A1 * | 11/2005 | Goodgame et al. | 378/4 |
| 2006/0072801 A1 * | 4/2006 | Bernard Deman et al. | 382/131 |
| 2007/0058771 A1 * | 3/2007 | Sauer et al. | 378/4 |
| 2010/0246751 A1 * | 9/2010 | Bruder et al. | 378/4 |
| 2012/0020448 A1 * | 1/2012 | Khare et al. | 378/4 |

FOREIGN PATENT DOCUMENTS

| WO | 9847103 A1 | 10/1998 |
|---|---|---|
| WO | WO 9847103 A1 * | 10/1998 |

OTHER PUBLICATIONS

Lee et al., "A Modified OSEM Algorithm for PET Reconstruction using wavelet Processing," 2005; Computer Methods and Programs in Biomedicine, Elsevier, Amsterdam, NL; 80(3) 236-245.

(Continued)

*Primary Examiner* — Alexander H Taningco

(57) ABSTRACT

An imaging system (10) comprises at least one radiation detector (20) disposed adjacent a subject receiving aperture (18) to detect radiation from a subject, receive the radiation and generate measured data. An image processor (38) iteratively reconstructs the detected radiation into image representations, in each reconstruction iteration the image processor (38) applies noise reduction algorithms to at least a difference between the measured data and a portion of a previous iteration image representation.

27 Claims, 4 Drawing Sheets

OTHER PUBLICATIONS

Levkovitz, et al., "The Design and Implementation of COSEM, an Interative Algorithm for Fully 3-D Listmode Data," 2001; IEEE Transactions on Medical Imaging, IEEE Service Center, Piscataway, NJ; 20(7).

Liang, "Implementation of Linear Filters for Iterative Penalized Maximum Likelihood SPECT Reconstruction," 1991; IEEE Transactions on Nuclear Science;38(2) Abstract.

Kontaxakis, et al, "Maximum Likelihood Algorithms for Image Reconstruction in Positron Emission Tomography," 1998; Radionucllides for Oncology-Current Status and Future Aspects, Mediterra Publishers, pp. 73-106.

Tanaka, "A Fast Reconstruction Algorithm for Stationary Positron Emission Tomography Based on a Modified EM Algorithm," 1987; IEEE Transactions on Medical Imaging, MI-6(2).

Wan, et al., "A Reconstruction Algorithm with Iterative Reconstruction-Reprojection and an FIR Filter," Information Options and Photonics Technology, Proc. of SPIE, 2005, vol. 5642, pp. 364-371.

Tanaka, "Intelligent Iterative Image Reconstruction with Automatic Noise Artifact Suppression," 1990 IEEE Nucl. Sci. Symp. and Med. Imag. Conf., pp. 1480-1486, Arlington, VA.

* cited by examiner

ITERATIVE RECONSTRUCTION WITH ENHANCED NOISE CONTROL FILTERING

CROSS REFERENCE TO RELATED APPLICATIONS

This application claims the benefit of U.S. provisional application Ser. No. 60/720,431 filed Sep. 26, 2005, which is incorporated herein by reference.

The present invention relates to the diagnostic imaging systems and methods. It finds particular application in conjunction with the Positron Emission Tomography (PET) and Single Photon Emission Tomography (SPECT) systems and will be described with particular reference thereto. It will be appreciated that the invention is also applicable to other medical imaging systems such as Computed Tomography systems (CT), and the like, and non-medical imaging systems.

Nuclear medicine imaging employs a source of radioactivity to image a patient. Typically, a radiopharmaceutical is injected into the patient. Radiopharmaceutical compounds contain a radioisotope that undergoes gamma-ray decay at a predictable rate and characteristic energy. One or more radiation detectors are placed adjacent to the patient to monitor and record emitted radiation. Sometimes, the detector is rotated or indexed around the patient to monitor the emitted radiation from a plurality of directions. Based on information such as detected position and energy, the radiopharmaceutical distribution in the body is determined and an image of the distribution is reconstructed to study the circulatory system, radiopharmaceutical uptake in selected organs or tissue, and the like.

Typically, in the iterative reconstruction technique, an estimate of the reconstructed volume of image data is forward projected onto the plane of the detector. The forward projected data is compared to the measured projection data. If the estimate of the reconstructed image were perfect, these two projections of data would match and there would be no difference. However, as the image is being built, there typically is a difference or error. The error or its inverse is then back-projected into the image volume to correct the volumetric image and create a new estimate for the next iteration.

Typically, the iterative reconstruction process continues until the measured and forward projected data sets match within an acceptable error. However, particularly in nuclear medicine, there are noise issues. That is, the measured projection is contaminated with noise and the forward projection is also contaminated with noise. As a practical matter, the noise will never match. As a result, the iterative process, if run for too long, can start to degenerate the reconstructed image. One technique is to filter the measured data or at a point during a reconstruction or filter the reconstruction images. While such filtering helps to reduce noise in an image, it also reduces image resolution.

The present invention provides a new and improved imaging apparatus and method which overcomes the above-referenced problems and others.

In accordance with one aspect, an imaging system is disclosed. At least one radiation detector is disposed adjacent a subject receiving aperture to detect radiation from a subject or passing through a subject, receive the radiation and generate measured data at a plurality of angles or a single angle. An image processor iteratively reconstructs the detected radiation into image representations, in each reconstruction iteration the image processor applies noise reduction algorithms to at least a difference between the measured data and a portion of a previous iteration image representation.

In accordance with another aspect, a method of imaging is disclosed. Radiation from a subject is detected. Measured data is generated. The detected radiation is iteratively reconstructed into image representations. In each reconstruction iteration noise reduction algorithms are applied to at least a difference between the measured data and a portion of a previous iteration image representation.

In accordance with another aspect, an imaging processor, which iteratively reconstructs input image data into image representations, is disclosed. A forward projector projects previous iteration image representation from an image memory, in which the iteration image representation is iteratively reconstructed. A first data manipulator manipulates the forward projected iteration image representation with a first noise reduction algorithm. A second data manipulator manipulates the input image data with a second noise reduction algorithm. A comparator compares the manipulated forward projected iteration image representation with the manipulated input image data and, based on the comparison, determines variance data. A third data manipulator manipulates the variance data with a third noise reduction algorithm. A back projector back projects the manipulated variance data into reconstructed variance data. A data updater updates the previous iteration image representation with the reconstructed variance data into reconstructed image data.

One advantage resides in reducing the image noise while minimizing the noise reduction impact on the original data.

Another advantage resides in better image resolution.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
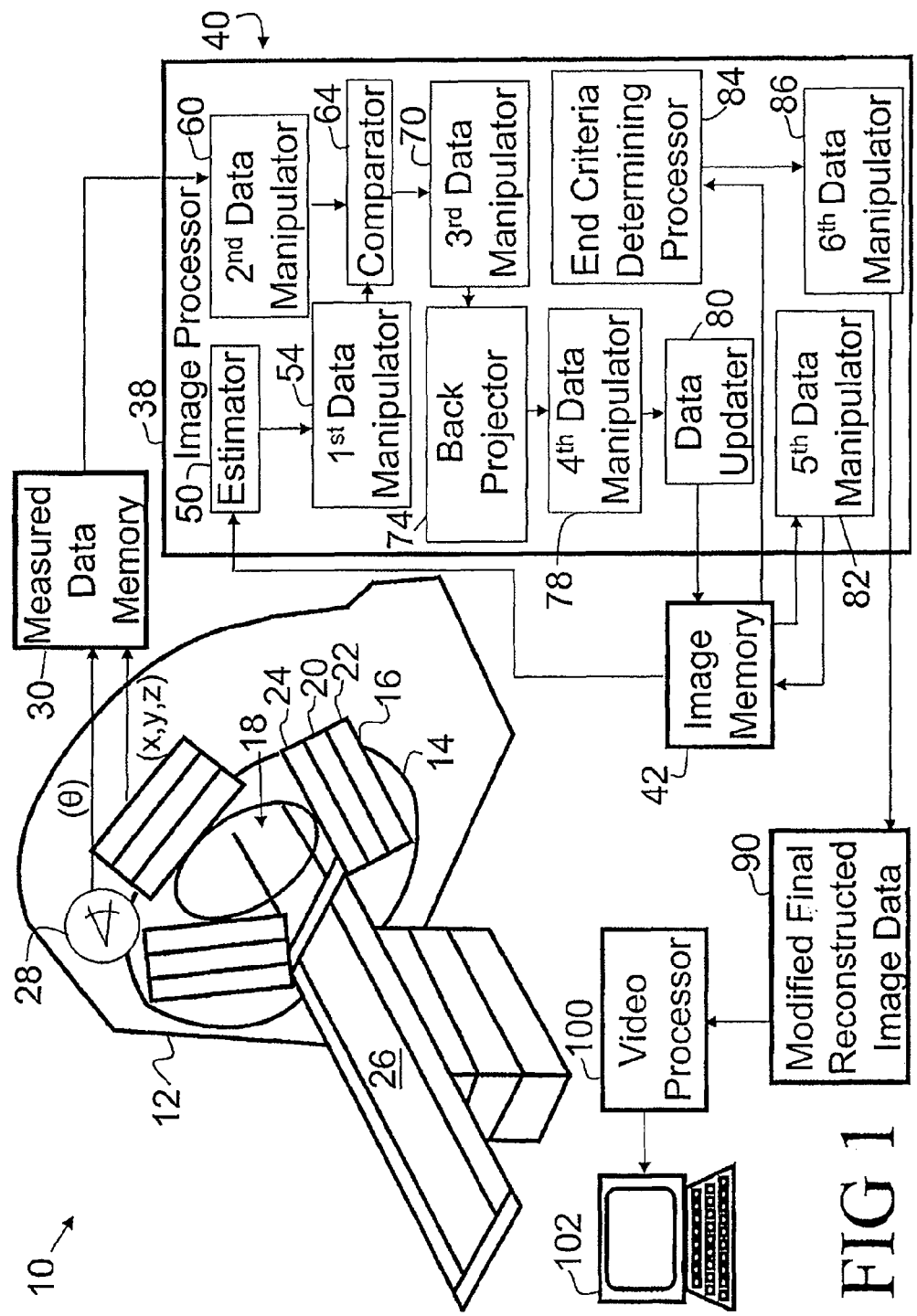
FIG. 1 is a diagrammatic illustration of an imaging system.

With reference to FIG. 1, a nuclear imaging system 10 typically includes a stationary gantry 12 that supports a rotatable gantry 14. One or more detection heads 16 are carried by the rotatable gantry 14 to detect radiation events emanating from a region of interest or examination region 18. Alternately, particularly in a PET scanner, the examination region is surrounded by a ring of stationary detectors. Each detection head includes two-dimensional arrays of detector elements or detector 20 such as a scintillator and light sensitive elements, e.g. photomultiplier tubes, photodiodes, and the like. Direct radiation signal to electrical converters, such as CZT elements, are also contemplated. Each head 16 includes circuitry 22 for converting each radiation response into a digital signal indicative of its location (x, y) on the detector face and its energy (z). The location of an event on the detector 20 is resolved and/or determined in a two dimensional (2D) Cartesian coordinate system with nominally termed x and y coordinates. However, other coordinate systems are contemplated. In one embodiment, a scatter grid and/or collimator 24 controls the direction and angular spread, from which each element of the detector 20 can receive radiation. Particularly in a SPECT scanner, the detector 20 limits the reception of radiation only along known rays. Thus, the determined location on the detector 20 at which radiation is detected and the angular position of the camera 16 define the nominal ray along which each radiation event occurred.

Typically, an object to be imaged is injected with one or more radiopharmaceuticals or radioisotopes and placed in the examination region 18 supported by a couch 26. Few examples of such isotopes are Tc-99m, Ga-67, and In-111. The presence of the radiopharmaceuticals within the object produces emission radiation from the object. Radiation is detected by the detection heads 16 which are able to be angularly indexed or rotated around the examination region 18 to collect the projection emission data at one or more selected projection directions. The projection emission data, e.g. the location (x, y), energy (z), and an angular position (θ) of each detection head 16 around the examination region 18 (e.g., obtained from an angular position resolver 28) are stored in a measured data memory 30.

With continuing reference to FIG. 1, an image processor 38 iteratively reconstructs a 3D image using noise reduction algorithms at different stages of the reconstruction via a noise reduction system or mechanism or means 40 as discussed in detail below. In one embodiment, the image processor 38 executes a Maximum Likelihood Expectation Maximization algorithm (MLEM). In preparation for the first iteration of the reconstruction process, an image memory 42 is initialized by loading the memory 42 with assumed or first estimate of the image. The image estimates are often characterized by uniform values inside the contour and zero values_outside the contour. Alternately, the availability of additional a priori information allows for more accurate first estimate.

Figure 2:
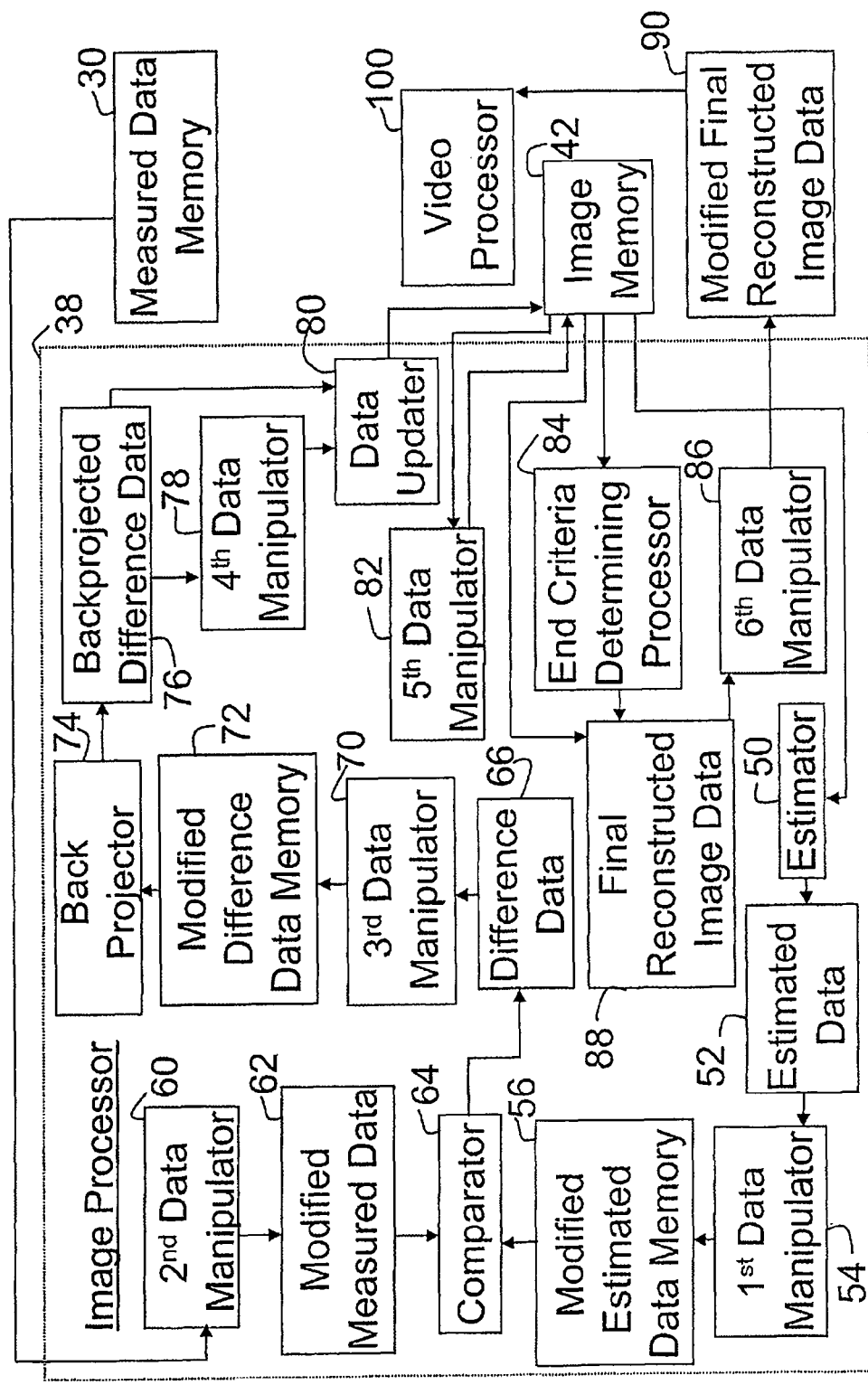
FIG. 2 is a diagrammatic illustration of a portion of the imaging system in detail.

With continuing reference to FIG. 1 and further reference to FIG. 2, the image processor 38 iteratively reconstructs 3D image representation and stores a current image iteration in the image memory 42. Each reconstruction iteration includes a forward projection or transformation operation and a back projection or transformation operation. A forward projector or estimator 50 creates current estimated projection data 52 from the current image iteration stored in the image memory 42. A first or estimated data manipulator 54 of the noise reduction mechanism 40 modifies or processes the estimated data 52 to reduce or eliminate noise in the estimated data 52. A modified estimated data is stored in a modified estimated data memory 56. A second or measured data manipulator 60 of the noise reduction mechanism 40 manipulates or processes the measured projection data from the measured data memory 30 to eliminate or reduce noise in the measured projection data. The modified measured projection data is stored in a modified measured data memory 62. A comparator 64 compares the modified measured projection data with the modified estimated data along the same direction to determine difference or variance data 66. Optionally, a third or difference data manipulator 70 of the noise reduction mechanism 40 modifies or processes the difference data 66 to reduce or eliminate noise in the difference data 66. A modified difference data is stored in a modified difference data memory 72. A back projector 74 back projects the modified difference data 72 to form a reconstructed difference image in a back projected or reconstructed difference image memory 76. Optionally, a fourth data manipulator 78 of the noise reduction mechanism 40 modifies or processes the reconstructed difference image in the reconstructed difference image memory 76 to reduce or eliminate noise in the reconstructed difference image. An image updater 80 updates the current image iteration in the image memory 42 with the reconstructed difference image of the reconstructed difference image memory 76. Optionally, a fifth or updated data manipulator 82 of the noise reduction mechanism 40 modifies or processes the reconstructed image data in the image memory 42 to reduce or eliminate noise in the reconstructed image data.

An end determining criteria processor 84 determines when to stop the iterative reconstruction process. If the differences fall below a preselected level, the iterative reconstruction process ends. Optionally, a sixth or final data manipulator 86 of the noise reduction mechanism 40 modifies or processes final reconstructed image data 88 to reduce or eliminate noise in the final reconstructed image data 88. The modified final reconstructed data is stored in a modified final reconstructed image data memory 90 which may be the same memory as image memory 42. Optionally, images retrieved from the final image memory may be filtered or manipulated, e.g. smoothed, edge enhanced, or the like, as is appropriate to the study and the preferences of the diagnostician. In this manner, each successive iteration is performed with the most recently updated image.

The examples of first, second, third, fourth, fifth and sixth data manipulators are any type of processors or algorithms capable of data manipulations to improve signal to noise ratio such as high pass filter, low pass filter, Gaussian, Median filter and Hanning filter. It is contemplated that all or some of the first, second, third, fourth, fifth and sixth data manipulators are the same type or different type data manipulators or filters, depending on the system characteristics. More specifically to a preferred embodiment, the first and second data manipulators apply matching or corresponding algorithms. The remaining algorithms may be different or eliminated.

A video processor 100 retrieves slices, projections, 3D renderings, and other image information from the modified final reconstructed image memory 90 and appropriately formats an image representation for display on one or more human viewable displays, such as a video monitor 102, printer, storage media, or the like. If the video processor repeatedly retrieves the selected image formation during reconstruction, the display will become clearer with each iteration as the reconstructed image converges on a final image.

Figure 3:
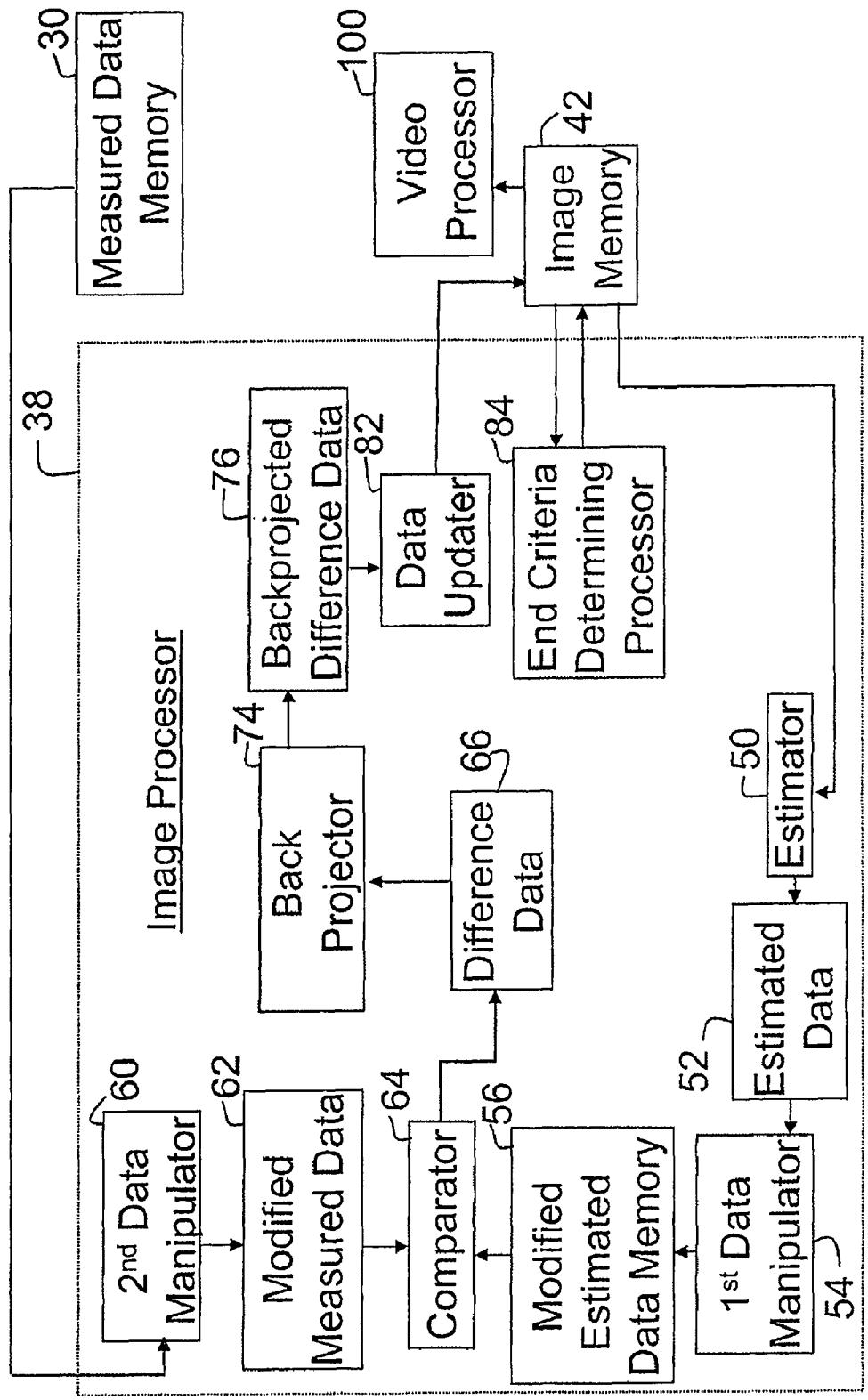
FIG. 3 is a diagrammatic illustration of another portion of the imaging system in detail.

With continuing reference to FIG. 2 and further reference to FIG. 3, in this embodiment, the optional third, fourth, fifth and sixth data manipulators 70, 78, 82, 86 are omitted from the noise reduction mechanism 40. Only the estimated projection data and the measured projection data are processed or manipulated via corresponding first and second data manipulators 54, 60. Generally, the MLEM Iterative Algorithm can be expressed as:

$$\lambda^{n+1} = \lambda^n \frac{\sum_j w_{ij} \frac{p_j}{\sum_l w_{lj} \lambda^n}}{\sum_j w_{ij}} \quad (1)$$

where $\lambda^n$ is the current estimate of the image, $p_j$ is the measured projection data, and $w_{ij}$ is the probability that a photon emitted from image space at position i is being detected at position j at the detector.

The MLEM iterative algorithm for dual data manipulation, in which the first and second data manipulators 54, 60 are used, can be expressed as:

$$\lambda^{n+1} = \lambda^n \frac{\sum_j w_{ij} \frac{F_2\{p_j\}}{F_1\left\{\sum_l w_{ij}\lambda^n\right\}}}{\sum_j w_{ij}} \quad (2)$$

where $F_1\{\ \}$ indicates filtering or processing or other noise reducing manipulating of the estimated projection data; and $F_2\{\ \}$ indicates filtering or processing or other noise reducing manipulating of the measured projection data.

In one embodiment, the same noise reduction filter is applied to the measured projection data and the estimated projection data. Applying a filter to the measured projection data helps to control the noise in the measured projection data. Applying the same filter in the estimated projection data tends to cancel the blurring effect of the previous filter.

In this manner, by applying the dual filtering technique, the random noise in the raw data and processing noise during reconstruction are reduced while the impact of filtering on the original signal is minimized.

Figure 4:
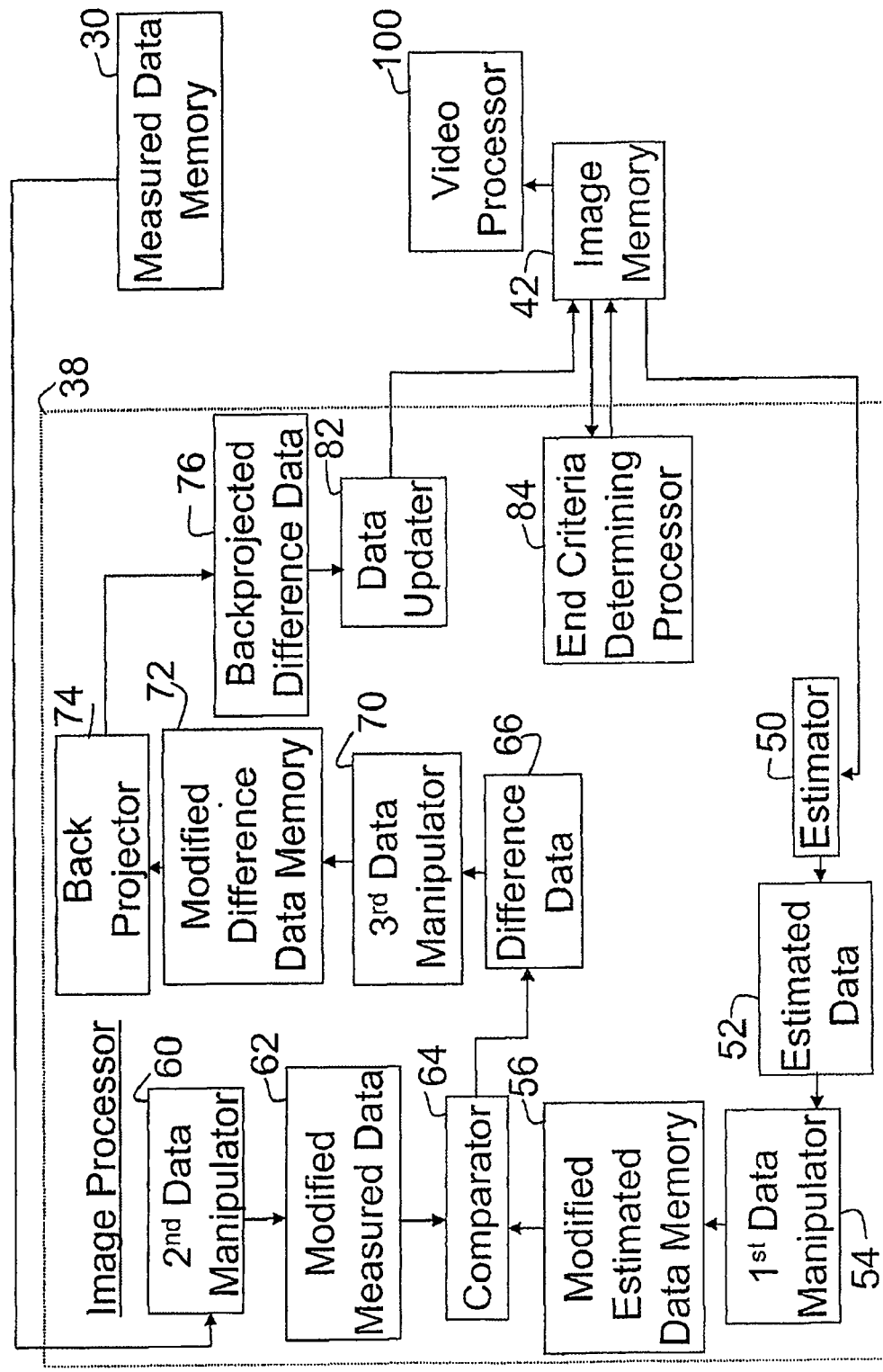
FIG. 4 is a diagrammatic illustration of yet another portion of the imaging system in detail.

With continuing reference to FIG. 2 and further reference to FIG. 4, in this embodiment, the fourth, fifth and sixth data manipulators 78, 82, 86 are omitted from the noise reduction mechanism 40. The measured projection data, the estimated projection data, and the difference data between the modified measured projection data and the modified estimated projection data are processed via corresponding first, second and third data manipulators 54, 60, 70.

The MLEM iteration algorithm, in which the third data manipulator 70 is used to process the difference data, can be expressed as:

$$\lambda^{n+1} = \lambda^n \frac{\sum_j w_{ij} F_3\left\{\frac{p_j}{\sum_l w_{ij}\lambda^n}\right\}}{\sum_j w_{ij}} \quad (3)$$

where $F_3\{\ \}$ indicates processing or filtering or other noise reducing manipulating of the difference data.

The MLEM Iterative Algorithm for triple data manipulation, in which the first, second and third data manipulators 54, 60, 70 are used, can be expressed as:

$$\lambda^{n+1} = \lambda^n \frac{\sum_j w_{ij} F_3\left\{\frac{F_2\{p_j\}}{F_1\left\{\sum_l w_{ij}\lambda^n\right\}}\right\}}{\sum_j w_{ij}} \quad (4)$$

where $F_1\{\ \}$ indicates filtering or processing or manipulating of the estimated projection data;
$F_2\{\ \}$ indicates filtering or processing or manipulating of the measured projection data; and
$F_3\{\ \}$ indicates filtering or processing or manipulating of the difference data.

In one embodiment, the image processor 38 executes an Ordered Subsets Expectation Maximization Algorithm (OSEM). The measured projection data is divided into subsets. The second data manipulator 60 modifies or processes one data subset at a time.

Of course it is also contemplated that the image processor 38 executes other alternative algorithms including Maximum A Posteriori (MAP), Algebraic Reconstruction Technique (ART), Iterative Filtered Back Projection (IFBP), and other like iterative algorithms.

Although described with reference to 3D reconstruction, the above methods and apparatuses are applicable to 2D and 1D image restoration where any combination of same or different filters or data manipulators described above is applicable to reduce or cancel the noise while preserving the image data.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An imaging system comprising:
   at least one radiation detector to detect radiation from a subject, receive the radiation and generate measured projection data; and
   an image processor which iteratively reconstructs the detected radiation into image representations, in each reconstruction iteration the image processor applies at least first and second noise reduction algorithms.

2. The system as set forth in claim 1, wherein the image processor is programmed to:
   apply the first noise reduction algorithm to the measured projection data.

3. The system as set forth in claim 2, wherein the image processor is further programmed to:
   process one of forward projection of a previous iteration image representation and a variance between the forward projection and the measured projection data with the second noise reduction algorithm.

4. The system as set forth in claim 1, wherein the image processor is programmed to:
   process a forward projection of a previous iteration image representation with a first noise reduction algorithm;
   process the measured projection data with a second noise reduction algorithm;
   process a variance between the forward projection data and the measured projection data with a third noise reduction algorithm.

5. The system as set forth in claim 4, wherein the at least two of the first, second and third noise reduction algorithms are the same type algorithms.

6. The system as set forth in claim 1, the detector is part of at least one of:
   a PET scanner;
   a SPECT scanner; and
   a CT scanner.

7. A method of imaging comprising:
   detecting radiation from a subject;
   generating measured data; and
   iteratively reconstructing the detected radiation into image representations, in each reconstruction iteration applying a first noise reduction algorithm to the measured data and a second noise reduction algorithm to at least a portion of a previous iteration image representation.

8. The method as set forth in claim 7, wherein the measured data includes projection data and the step of reconstructing includes:
    forward projecting a previous iteration image representation from an image memory in which the iteration image representation is iteratively reconstructed;
    comparing the processed forward projected iteration image representation with the filtered measured projection data;
    based on the comparison, determining variance data;
    back projecting the determined variance data into reconstructed variance data; and
    updating the previous iteration image representation with the reconstructed variance data.

9. The method as set forth in claim 8, wherein the step of reconstructing further includes:
    processing the determined variance data with a third noise reduction algorithm before back projecting.

10. The method as set forth in claim 8, wherein the step of reconstructing further includes at least one of:
    processing the forward projected iteration image representation with the second noise reduction algorithm; and
    processing the measured projection data with the first noise reduction algorithm.

11. The method as set forth in claim 8, wherein the step of reconstructing further includes:
    processing the reconstructed variance data after back-projecting with a third noise reduction algorithm.

12. The method as set forth in claim 7, wherein the step of reconstructing includes:
    comparing each iteration image representation with an end criteria;
    terminating the iterative reconstruction in response to the end criteria being met; and
    processing a final iterative image representation with a third noise reduction algorithm.

13. The method as set forth in claim 7, wherein the step of iterative reconstructing includes:
    forward projecting a current iteration image representation;
    applying the second noise reduction algorithm to the forward projected iteration image representation and the first noise reduction algorithm to the measured data;
    determining a variation between the filtered noise reduced forward projected image representation and the filtered measured data; and
    modifying the current iteration image representation in accordance with the variation.

14. The method as set forth in claim 13, wherein the iterative reconstructing applied is:

$$\lambda^{n+1} = \lambda^n \frac{\sum_j w_{ij} \frac{F_2\{p_j\}}{F_1\left\{\sum_l w_{ij}\lambda^n\right\}}}{\sum_j w_{ij}}$$

where $F_1\{\ \}$ indicates filtering or processing or other noise reducing manipulating of the forward projected data, $F_2\{\ \}$ indicates filtering or processing or other noise reducing manipulating of the measured data, $\lambda^n$ is a current estimate of the image, $p_j$ is the measured projection data, and $w_{ij}$ is the probability that a photon emitted from an image space at position I is being detected at position j at the detector.

15. An imaging system for performing the method of claim 7, comprising:
    a radiation detector which performs the detecting and generating steps of claim 7; and
    an image processor which performs the iterative reconstructing step of claim 7.

16. An image processor, which iteratively reconstructs input image data into image representations, the image processor comprising:
    a forward projector, which forward projects previous iteration image representation from an image memory, in which the iteration image representation is iteratively reconstructed;
    a first data manipulator, which manipulates the forward projected iteration image representation with a first noise reduction algorithm;
    a second data manipulator, which manipulates the input image data with a second noise reduction algorithm;
    a comparator, which compares the manipulated forward projected iteration image representation with the manipulated input image data and, based on the comparison, determines variance data;
    a back projector, which back projects the variance data into reconstructed variance data; and
    a data updater, which updates the previous iteration image representation with the reconstructed variance data into reconstructed image data.

17. The processor as set forth in claim 16, wherein the first and second noise reduction algorithms are the same type of the algorithms.

18. The processor as set forth in claim 16, wherein the image processor further includes:
    a third data manipulator, which manipulates the variance data before the back projecting with a noise reduction algorithm.

19. The processor as set forth in claim 18, wherein the image processor further includes:
    a fourth data manipulator, which manipulates the reconstructed variance data after the back projecting with a noise reduction algorithm.

20. A method of forming a medical image comprising:
    receiving sets of measured medical image data of a patient;
    iteratively reconstructing the sets of medical image data into image representations, in each reconstruction iteration applying a first noise reduction algorithm to one of the received sets of medical image data and a second noise reduction algorithm to a portion of a previous iteration image representation.

21. The method of claim 20 wherein the iterative reconstruction further comprises filtering the iteratively reconstructed medical image for noise prior to forming a final iterative image.

22. The method of claim 21 wherein the filtering noise step is performed using the same type of algorithms.

23. An image processor programmed to perform the method of claim 20.

24. An image processing system including a processor programmed to:
    (a) filter a set of image data with a first noise reduction algorithm;
    (b) update an iteratively reconstructed image representation with the filtered set of image data;
    (c) iteratively repeat steps (a) and (b) to improve the iteratively reconstructed image representation.

25. The image processing system of claim 24, wherein step (b) includes applying a second noise reduction algorithm.

26. The image processing system of claim 24, wherein each set of image data includes projection data and step (b) includes:
  forward projecting the iteratively reconstructed image representation to generate forward projected data;
  comparing the filtered set of image data and the forward projected data to generate image update data;
  updating the iteratively reconstructed image representation with the image update data; and
  filtering one of the forward projection data and the image update data with a second noise reduction algorithm.

27. The image processing system of claim 24, wherein the processor is further programmed to:
  filter the iteratively reconstructed image representation with a second noise reduction algorithm.

* * * * *